US010041029B2

(12) United States Patent
Dujardin et al.

(10) Patent No.: US 10,041,029 B2
(45) Date of Patent: Aug. 7, 2018

(54) VESSEL WITH ADJUSTABLE SIDE DRAIN

(75) Inventors: Patrick Dujardin, Outgaarden (BE);
Steven Vanhamel, Velm (BE);
Matthew Kusz, Minneapolis, MN (US)

(73) Assignee: PALL LIFE SCIENCES BELGIUM,
Hoegaarden (BE)

( * ) Notice: Subject to any disclaimer, the term of this patent is extended or adjusted under 35 U.S.C. 154(b) by 746 days.

(21) Appl. No.: 13/575,716

(22) PCT Filed: Jan. 28, 2011

(86) PCT No.: PCT/US2011/022914
§ 371 (c)(1),
(2), (4) Date: Oct. 12, 2012

(87) PCT Pub. No.: WO2011/094534
PCT Pub. Date: Aug. 4, 2011

(65) Prior Publication Data
US 2013/0037123 A1    Feb. 14, 2013

Related U.S. Application Data

(60) Provisional application No. 61/299,190, filed on Jan. 28, 2010.

(51) Int. Cl.
F17D 1/00 (2006.01)
C12M 1/00 (2006.01)
C12M 1/26 (2006.01)

(52) U.S. Cl.
CPC ............ *C12M 23/14* (2013.01); *C12M 23/28* (2013.01); *C12M 33/00* (2013.01); *Y10T 137/0402* (2015.04); *Y10T 137/598* (2015.04)

(58) Field of Classification Search
CPC ........... F16L 5/06; B01F 5/0218; B01F 5/025; Y10T 137/8275

(Continued)

(56) References Cited

U.S. PATENT DOCUMENTS 266,894 A * 10/1882 Robertson ................ 222/153.03
307,325 A * 10/1884 Pattison ........................ 137/579

(Continued)

FOREIGN PATENT DOCUMENTS

EP           1099471 A1    5/2001
WO      WO2009048442 A1    4/2009

OTHER PUBLICATIONS

The American Heritage Dictionary of the English Language https://www.andictionary.com/word/search.html?q=drain drain (drān) 2 Pages Printed Apr. 24, 2015.

*Primary Examiner* — Craig Schneider
*Assistant Examiner* — Angelisa L Hicks
(74) *Attorney, Agent, or Firm* — King & Schickli, PLLC

(57) ABSTRACT

An apparatus for processing fluid includes a vessel provided with a sidewall including a passage and at least partially defining an interior compartment. A drain tube positioned in the interior compartment may drain fluid through the passage in the sidewall. The drain tube may be angled, and arranged such that the end in the interior compartment may be adapted for movement as the result of manipulation of a structure, such as a coupler, external to the interior compartment. Accordingly, the drain tube may be positioned along the sidewall at a reference point for movement between a first position for draining fluid above the reference point and a second position for draining fluid below the reference point. An indexing feature may also be provided for incrementally adjusting the position of the drain tube, along with an associated tool to facilitate the adjustment. Related methods are also disclosed.

22 Claims, 6 Drawing Sheets

(58) Field of Classification Search
USPC ............... 137/577, 579, 551, 553, 556, 559; 422/225
See application file for complete search history.

(56) References Cited

U.S. PATENT DOCUMENTS

| | | | | |
|---|---|---|---|---|
| 356,511 | A * | 1/1887 | Turner | F16K 37/0058 137/556 |
| 378,812 | A * | 2/1888 | Tyler | 222/159 |
| 618,532 | A * | 1/1899 | Beman | G01F 11/266 137/577 |
| 2,041,296 | A * | 5/1936 | Gilmore | F24D 19/1003 137/132 |
| 2,543,883 | A * | 3/1951 | Von Saspe | B28C 7/122 137/552 |
| 2,578,000 | A * | 12/1951 | Cronk | 222/464.3 |
| 3,658,080 | A * | 4/1972 | Mitchell | 137/1 |
| 4,276,856 | A * | 7/1981 | Dent et al. | 122/382 |
| 4,465,095 | A * | 8/1984 | Lindberg | F02M 25/028 123/25 L |
| 4,492,186 | A * | 1/1985 | Helm | 122/382 |
| 4,636,313 | A | 1/1987 | Vaillancourt | |
| 4,905,900 | A * | 3/1990 | Scharton et al. | 239/99 |
| 4,936,837 | A | 6/1990 | Wexler | |
| 5,137,052 | A * | 8/1992 | Baumgart | F16K 31/60 116/277 |
| 5,360,556 | A * | 11/1994 | Ball et al. | 210/804 |
| 6,722,705 | B2 | 4/2004 | Korkor | |
| 7,225,824 | B2 | 6/2007 | West et al. | |
| 2001/0056257 | A1 | 12/2001 | Drasler et al. | |
| 2002/0015671 | A1 | 2/2002 | Lee | |
| 2002/0072702 | A1 | 6/2002 | Quay | |
| 2005/0032211 | A1 | 2/2005 | Shaaltiel | |
| 2005/0062283 | A1 * | 3/2005 | Hawkinson et al. | 285/139.1 |
| 2008/0254471 | A1 | 10/2008 | Bordano | |

\* cited by examiner

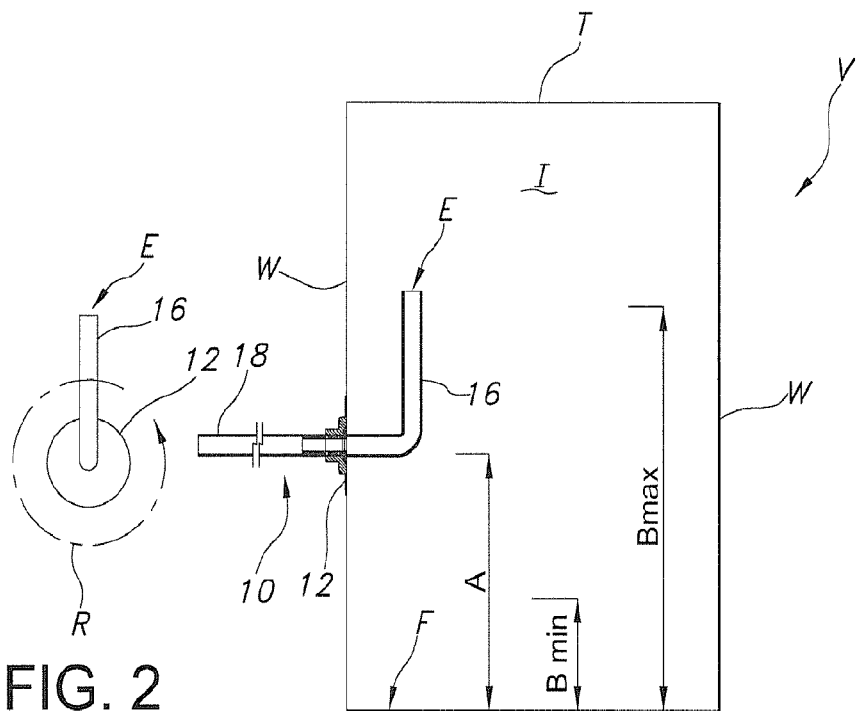
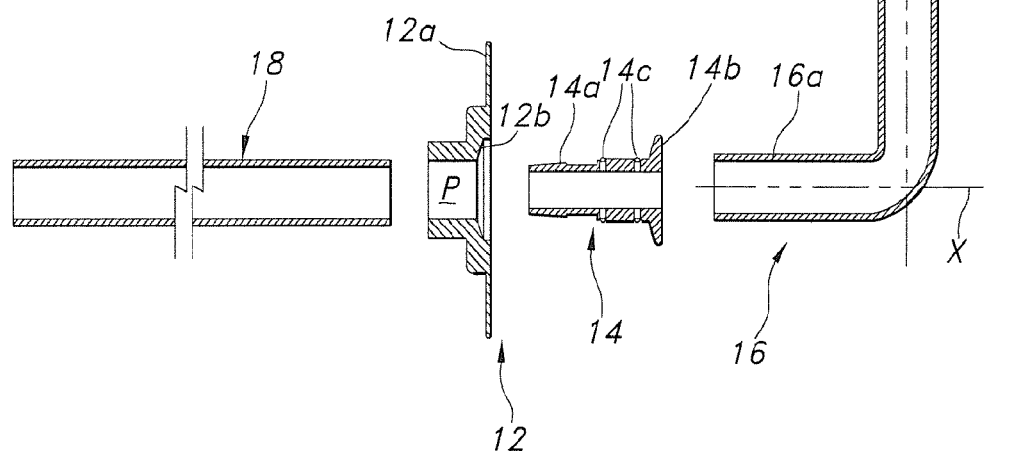
FIG. 2
FIG. 1
FIG. 3

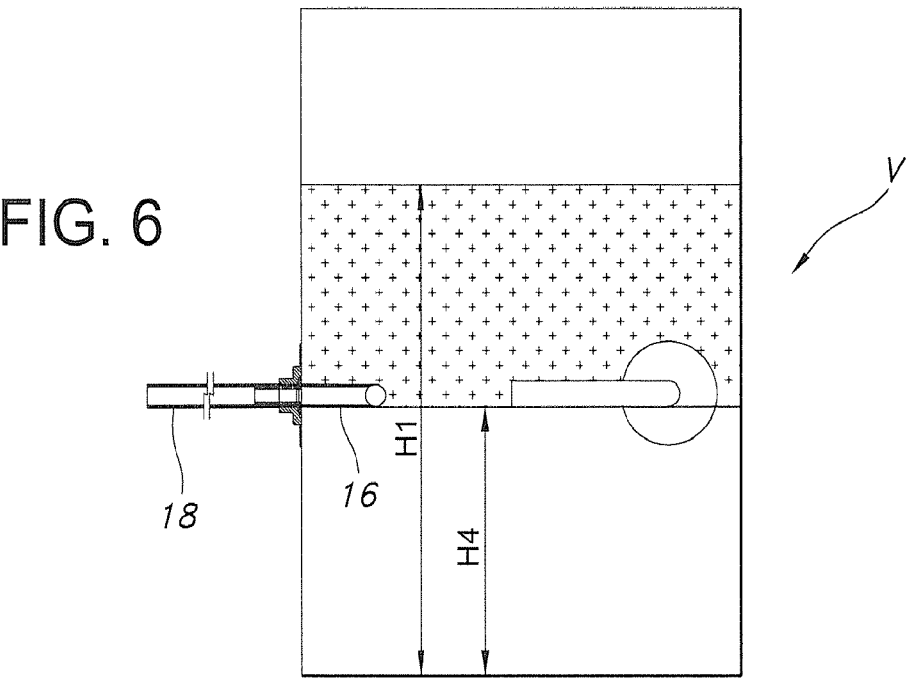
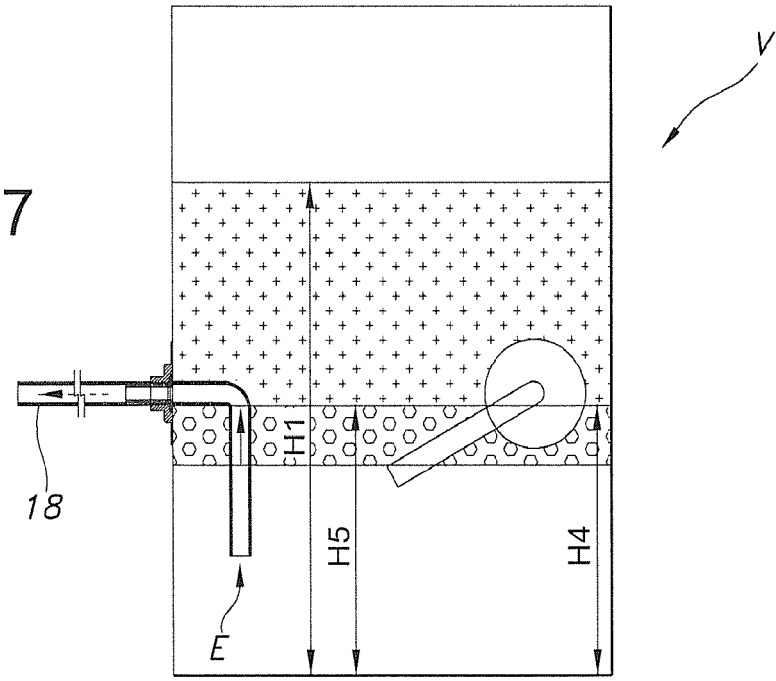

VESSEL WITH ADJUSTABLE SIDE DRAIN

This application claims the Benefit of U.S. Provisional Patent App. Ser. No. 61/299,190, filed on Jan. 28, 2010, the disclosure of which is incorporated herein by this reference.

TECHNICAL FIELD

The present invention relates generally to fluid processing and, more specifically, to a vessel including an adjustable side drain.

BACKGROUND OF THE INVENTION

Fluid processing applications typically employ vessels for at least temporarily receiving and containing the fluid, which is typically a liquid. For example, in the course of bioprocessing, hermetically sealed bags formed of flexible plastic film are often used for bulk intermediate storage, cell culture re-suspension, viral inactivation, final formulation, final fill, or as bioreactors. In any case, such vessels or bags almost universally include one or more drains for use in recovering the fluid at some point during processing or after its completion.

Oftentimes, different applications or users of such vessels dictate that a drain is provided in the side of the vessel at a specific height. This could lead to the production of various types of vessels adapted for the particular purpose of the end user. However, with that approach, manufacturers of the vessels would thus need to await an order before manufacturing the vessel with the drain, or stockpile quantities of vessels having the most desirable drain positions in anticipation of possible future customer needs. As can be appreciated, neither practice is considered particularly efficient or effective from a cost standpoint.

Thus, a need is identified for a manner of providing an improved side drain for a vessel, such as a mixing bag. The drain would be capable of use in addressing a variety of different requirements for the vessels, and would also be relatively easy to create and implement. Overall, use of the novel side drain would thus lead to a simplification of the manufacturing process and a concomitant reduction in the expense associated with manufacturing vessels, such as flexible bags.

SUMMARY OF THE INVENTION

One aspect of the disclosure pertains to an apparatus for forming a drain in a vessel including a sidewall at least partially defining an interior compartment for receiving a fluid. The apparatus may comprise an angled or bent drain tube for withdrawing fluid from the interior compartment. The drain tube is capable of rotating within the interior compartment. A connector is also provided for connecting to the sidewall of the vessel. The connector is adapted for supporting the angled drain tube.

In one possible embodiment, a coupler is adapted for coupling with a first end of the drain tube. Preferably, the coupler is positioned in the connector. The apparatus may include at least one sealing element for sealing the coupler with the connector, and may further include a drain tube external to the interior compartment, such that the coupler is adapted for coupling with the external drain tube. The coupler may include a peripheral flange for mating with a recess of the connector.

The angled drain tube may comprise a first leg extending generally perpendicular to a second leg. Preferably, the second leg is longer than the first leg. Most preferably, a distance from a floor of the vessel to the connector substantially matches a length of the second leg of the drain tube.

Another aspect disclosed herein is an apparatus for forming a connection with a drain tube external to a vessel including a sidewall at least partially defining an interior compartment for receiving a fluid. The sidewall includes a connector, and the apparatus comprises a coupler for forming a sealing engagement with the connector and having a first end adapted for engaging the external drain tube. An angled drain tube is connected to the coupler and for positioning in the interior compartment.

A further aspect of the disclosure is an apparatus for use in processing a fluid. The apparatus comprises a vessel adapted for receiving the fluid, the vessel having a sidewall including a passage and at least partially defining an interior compartment. A drain tube is provided for positioning at least partially in the interior compartment and draining fluid therefrom through the passage.

In one possible embodiment, the apparatus includes a coupler adapted for coupling with a first end of the drain tube in the interior compartment. Preferably, the coupler is positioned at least partially within a tubular connector connected to the sidewall of the vessel. At least one sealing element may be provided for sealing the coupler with the connector. A second drain tube external to the interior compartment may be provided, and the coupler may be further adapted for coupling with the external drain tube. The coupler may also include a peripheral flange for mating with a recess of the connector.

The drain tube may comprise a first leg extending generally perpendicular to a second leg. Preferably, the second leg has a length greater than the first leg. The drain tube may also connect with a tubular connector connected to the sidewall of the vessel.

A first end of drain tube may include an inlet for receiving fluid in the interior compartment. This first end including the inlet for receiving fluid in the interior compartment preferably does not lie on the same linear axis as a second end of the drain tube. As such, the tube may be considered angled or curved.

Still a further aspect of the invention is an apparatus for forming a drain for a fluid. The apparatus comprises a vessel adapted for receiving the fluid and including a sidewall at least partially defining an interior compartment. A drain tube is connected to the sidewall and extending in the interior compartment, and includes a portion having a longitudinal axis generally aligned with a plane of the sidewall. Preferably, the longitudinal axis is generally parallel to the plane of the sidewall, which is more preferably generally vertical when the vessel is filled with fluid.

An additional aspect of this disclosure pertains to an apparatus for forming a fluid drain. The apparatus comprises a vessel adapted for receiving a fluid and including a top wall and a bottom wall connected by at least one flexible sidewall so at to at least partially define an interior compartment for receiving a fluid. A drain tube is connected to the flexible sidewall and projects into the interior compartment of the vessel.

Preferably, the apparatus further includes a connector connected to the sidewall of the vessel, and wherein the drain tube is mounted for rotation relative to the connector. The apparatus may include a coupler for coupling the drain tube to the connector. Preferably, the drain tube includes a first portion extending at an angle relative to a second portion and, most preferably, the angle comprises about 90°.

Still another aspect of the disclosure is an apparatus for forming a drain for a fluid. The apparatus comprises a vessel including a sidewall at least partially forming an interior compartment for receiving the fluid. A drain tube is connected to the sidewall at a reference point, and includes having an inlet adapted for movement between a first position for draining fluid at or above the reference point and a second position for draining fluid at or below the reference point.

Still a further aspect of the disclosure is an apparatus for forming a drain for a fluid. The apparatus comprises a vessel adapted for receiving the fluid and including a sidewall. The apparatus further includes a drain tube rotatably supported by the sidewall and having an inlet, wherein rotation of the drain tube relative to the sidewall moves the inlet in a plane parallel to the sidewall.

In any of the embodiments of the invention, the drain tube may be L-shaped and is preferably rigid. The drain tube may also be curved. The vessel may comprise a flexible bag. The apparatus in any of the disclosed embodiments may further include: (1) means for indexing the drain tube relative to the vessel (which may include at least one identification external to the interior compartment corresponding to the position of the drain tube relative to the vessel; or (2) means for forcing fluid to flow through the drain tube (such as a pump).

Yet another disclosed aspect is an apparatus for forming a passage for a fluid. The apparatus comprises a vessel including a wall at least partially defining an interior compartment for receiving the fluid. A tube projects into the interior compartment of the vessel, and is arranged to rotate relative to the wall of the vessel. At least one identification corresponds to the position of the drain tube relative to the vessel during rotation.

In one possible embodiment, the apparatus further includes an indicator for indicating the position of the drain tube relative to the at least one identification. The apparatus may further include a grip associated with the drain tube. Preferably, the grip comprises a flange adapted for receiving a tool.

This disclosure also provides for a method of processing a fluid using the apparatus as disclosed, as well as a method of forming a vessel having a sidewall. The forming method comprises providing the vessel including a drain tube connected to the sidewall at a reference point. The drain tube includes an inlet adapted for movement between a first position for draining fluid at or above the reference point and a second position for draining fluid at or below the reference point. The method may further include the step of rotating the drain tube, such as from the first position to the second position or vice-versa. The steps of draining or pumping fluid through the tube may also be performed.

A final aspect of the disclosure mentioned herein is a method of fluid processing. The method comprises providing a vessel including a drain tube having an inlet positioned in an interior compartment of the vessel. The method further includes the step of raising or lowering the inlet by rotating the drain tube.

BRIEF DESCRIPTION OF THE DRAWING FIGURES

FIG. 1 is a schematic side view of a vessel with an adjustable drain according to one aspect of the disclosure;

FIG. 2 is a schematic end view of the drain tube inside the vessel;

FIG. 3 is an exploded, cross-sectional view of an assembly including the drain tube;

FIGS. 4-10 are schematic views illustrating various possible modes of use of the adjustable side drain according to the disclosure;

DETAILED DESCRIPTION OF THE INVENTION

Figure 4:
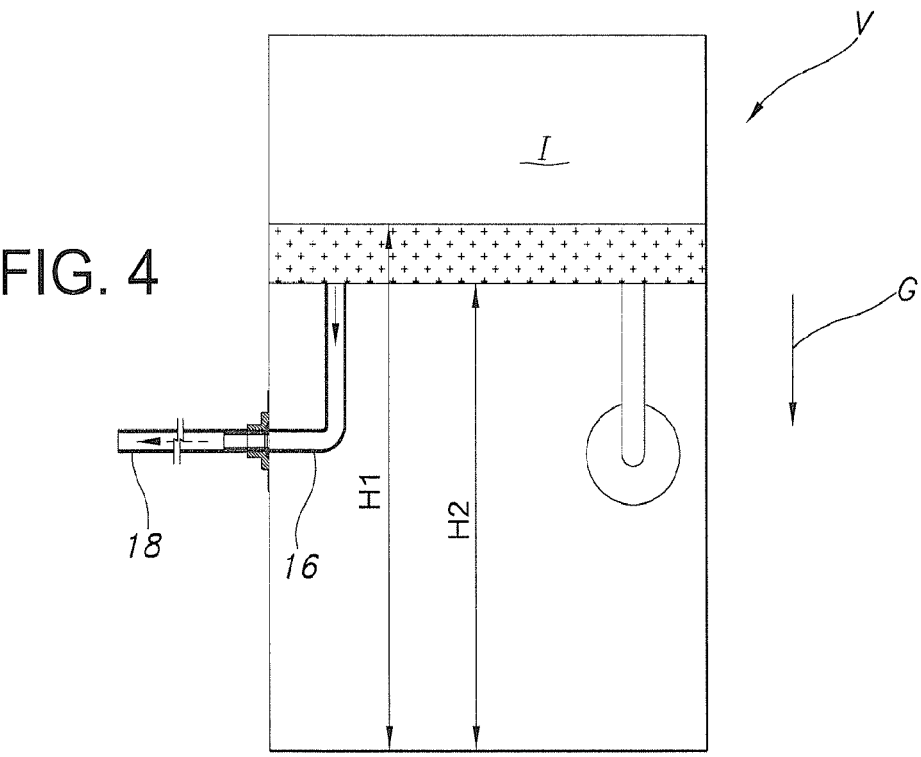

Reference is now made to FIGS. 1, 2, and 3, which together illustrate one possible embodiment of an adjustable drain 10 for a vessel V. Preferably, this vessel V comprises a disposable tank or bag of the type used in processing fluids, including under sterile conditions, such for preparing biological agents, pharmaceutical preparations, or the like. In the most preferred embodiment, the vessel V comprises one or more sidewalls W that fully or at least partially define the interior compartment I for receiving a fluid. The one or more sidewalls W are preferably made of a thin, flexible, plastic film, which means the resulting vessel V can be collapsed or folded and, when filled, may adapt to the shape dictated by the fluid in the interior compartment I. The sidewall W may be contrasted with the top wall T and the bottom wall M, which also defines a floor F along the interior compartment I. When the container comprises a flexible bag, it may be necessary or desirable to provide a support structure, such as a rigid outer container (not shown), for supporting the bag such that the one or more sidewalls W are oriented in a generally vertical direction. Impellers, spargers, or sensors may also be incorporated into the vessel V, as described in U.S. Pat. Nos. 7,481,572 and 7,384,027, the disclosures of which are incorporated herein by reference.

With continued reference to FIGS. 2 and 3, the adjustable drain 10 in the illustrated embodiment attaches to a portion of one sidewall W of the vessel V (as contrasted with the top wall T or the bottom wall M). Preferably, a connector 12 connected to this vessel sidewall W includes a passage P that, in the unobstructed condition, forms a port or opening from the exterior of the vessel V into the interior compartment I. This passage P is adapted for receiving a coupler 14 for connecting at one end with a drain tube 16 in fluid communication with the interior compartment I of the vessel V, preferably at an inlet E (which may be the end of the tube and entirely open to fluid flow, perforated with one or more openings, or both). However, it is possible to omit the connector 12 and/or coupler 14 such that the drain tube 16 extends through an opening forming a passage in the vessel sidewall W in a sealed fashion. It is also possible to combine one or more of these parts into a single structure while retaining the basic functionality.

For reasons that will be better understood upon reviewing the discussion that follows, at least the portion of drain tube 16 in the interior compartment I is arranged to have an angular configuration (with angular meaning that the tube is not linear, but not necessarily defining a precise or fixed angular relationship, and covering the situation where the tube is curved or bent). Most preferably, this tube 16 includes a first portion including the inlet E, such as leg 16a, with a longitudinal axis X perpendicular to the plane of the sidewall W and a second portion, such as leg 16b, having a longitudinal axis Y that extends in a direction parallel to this plane. Thus, as should be appreciated, these axes X, Y are generally orthogonal, and render the tube 16 generally L-shaped. However, it is possible to use other angled configurations, such as bends or curves, without departing from the broadest aspects of this disclosure. In such cases, it should be appreciated that the distal or inlet E end of the tube 16 is not provided on the same linear axis as the proximal or opposite end of the tube.

The opposite end of the coupler 14 may be adapted for connecting to a structure outside the interior compartment I, such as for example a stopper or plug prior to use (and preferably such that a sterile condition may be maintained in the vessel V) or a second external drain tube 18 for furthering the conveyance of the drained fluid. In such case, this end of the coupler 14 preferably includes a projection 14a (such as a barb) or is otherwise arranged for engaging this exterior drain tube 18 in a fluid-tight manner. The end of this drain tube 18 opposite the end associated with coupler 14 may be arranged to deliver the fluid to any desired location or device, including possibly another vessel for additional processing.

For purposes of being secured to the vessel V, the connector 12 may include a peripheral mounting flange 12a. This flange 12a includes substantially planar upper and lower faces adapted for connecting to the sidewall W adjacent a passage or opening therein, such as by welding, bonding, or other type of secure and substantially permanent connection. Adjacent to the interior compartment, this flange 12a bounds the inner end of the passage P formed in the connector 12. If present, the external drain tube 18 at the other end of the passage P is preferably oversized, and thus may abut with the adjacent surface of the connector 12.

The relative position of this end of the coupler 14 external to the vessel V may be controlled by a flange 14b adapted to mate in seating engagement with a matching recess 12b formed in the portion of the connector 12 facing the interior compartment I of the vessel V. Together with the oversized end of the external drain tube 18 or like structure, this flange 14b serves to capture the coupler 14 within the passage P. The coupler 14 may also include one or more sealing elements 14c, such as O-rings, mounted in a corresponding indentation (probably annular) or otherwise integrally formed. These sealing elements 14c are positioned such that, when the flange 14b is seated in the recess 12b, these sealing elements form a fluid impervious seal, but still allow for the coupler 14 to rotate freely relative to the connector 12.

In addition to interfacing with the connector 12, the coupler 14 as mentioned above also securely connects with the adjacent end of the first leg 16a of drain tube 16 in the interior compartment I. This connection is preferably done in a manner that not only forms a fluid tight seal, but also one that supports the drain tube 16 in a manner such that any rotation of the coupler 14 is transmitted to this drain tube 16. For instance, such a connection may be achieved by integrally forming the parts, such as through molding or welding, or by using a friction or interference fit. Regardless of the manner of connection, it may be desirable in certain embodiments that rotational movement can be transmitted from outside the vessel V to the drain tube 16 in the interior compartment I.

Thus, with reference to FIGS. 1 and 2 together, it can be understood that the angled interior drain tube 16 may be rotated substantially 360° (note arcuate action arrow R) remotely from the interior compartment I, such as by rotating the external tube 18, which in turn rotates coupler 14 connected to this tube. Using the external tube 18 as a dial in this manner moves the end E of the angled drain tube 16 from a maximum height $B_{max}$ corresponding to the twelve o'clock position in the illustrated orientation in the interior compartment I, to a minimum height $B_{min}$ corresponding to the six o'clock position, and to any point between. The axis of rotation is formed by the longitudinal axis X of the first leg 16a of the drain tube 16, which is at fixed height A in the interior compartment I as the result of the selected positioning of the associated connector 12.

Some of the benefits and advantages arising from use of the drain 10 described above are best understood with reference to FIGS. 4-10. FIG. 4 illustrates the drain 10 with the interior or first drain tube 16 arranged as shown in FIG. 1 (and as also shown by a front schematic view of the drain for purposes of illustrating the relative movement only), with the second leg 16b extending in a direction generally opposite the direction of gravity G (or vertically). When so oriented, fluid at a level $H_1$ in the vessel V flows via gravitational force through the end of this drain tube 16, through the passage formed by coupler 14, and out to the exterior via the external drain tube 18. This evacuation will occur until the fluid surface is level with the inlet of the interior tube 16, as shown by height $H_2$. The fluid is shown as being visually stratified for purposes of illustration only.

Figure 5:
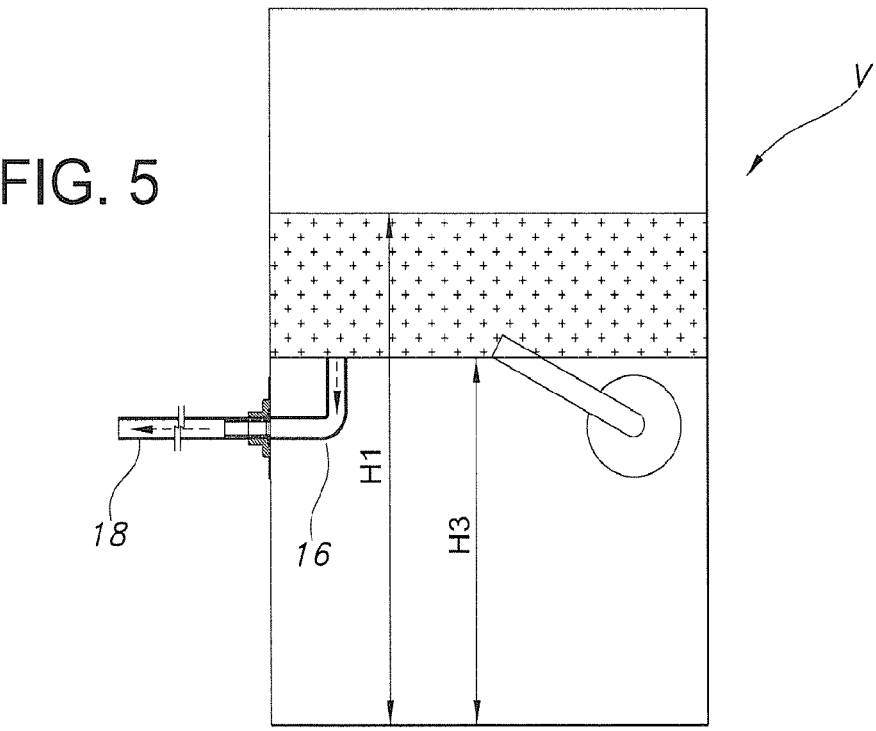

Given the ability of the coupler 14 to rotate relative to the connector 12, it should be appreciated that the drain 10 may be manipulated to reposition the drain tube 16 in the interior compartment I as desired for a particular fluid recovery operation. For instance, if it is desired to recover fluid to a certain level less than the height $H_2$ of the inlet E of the interior drain tube 16 in the fully vertical orientation, this tube may be rotated to a desired position, such as through the manipulation of the external tube 18. In this intermediate position, as shown in FIG. 5, it can be understood that fluid would flow through the inlet of the first tube 16 through connector 14 and second tube 18, until the height reaches the point where the fluid no longer enters the inlet, as identified by height $H_3$ (which of course corresponds to the lowermost edge of the inner surface of the tube 16, adjacent the inlet).

FIG. 6 shows the first drain tube 16 reoriented such that the longitudinal axis of the second leg 16b is substantially aligned in the same plane as the longitudinal axis of the first leg 16a. In this manner and using only gravity, the fluid may be withdrawn to any selected height between height $H_2$ and height $H_4$. This is generally the lowest position in which fluid evacuation may be meaningfully achieved solely by gravity.

Figure 8:
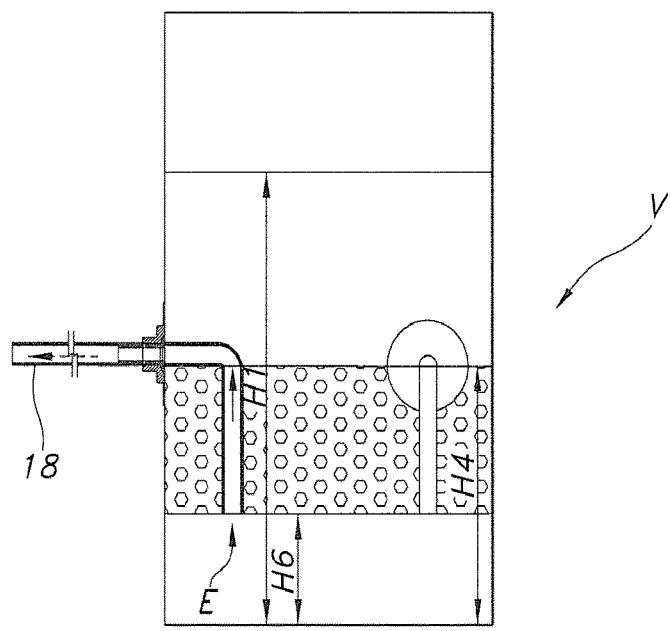

Despite this limitation on free flow, it should be understood that the first drain tube 16 may continue to be rotated to a position in which its inlet is below height $H_4$ corresponding to the plane parallel to the longitudinal axis of the first leg 16a, as shown in FIG. 7. In this position, fluid evacuation requires a form of force or leverage, either by way of increasing the pressure within the interior compartment I of the vessel V, or decreasing the pressure exterior to the interior compartment in a manner that causes fluid to be evacuated through the tube 16. The latter may be achieved by using a means for forcing fluid through the tube 16, such as by way of a conventional pump (not shown) or the like, or even by manual siphoning. The lowest position of the interior drain tube 16 is shown in FIG. 8, as corresponding to a height $H_6$, which is the minimum level of evacuation that may be achieved using an auxiliary means (at least until the inner end E of the tube 16 is no longer submerged).

It should be appreciated that the maximum and minimum working heights of the interior drain tube 16 may be altered based upon the relative positioning of the connector 12 along the sidewall W, as well as the length, orientation (e.g., angle or bend) and, to some extent, the shape of the second leg 16b. For instance, positioning the connector 12 along a lowermost portion of the sidewall W may allow fluid to be substantially evacuated from the interior compartment with the drain tube 16 having its inlet E adjacent to or in contact with the floor F.

Figure 9:
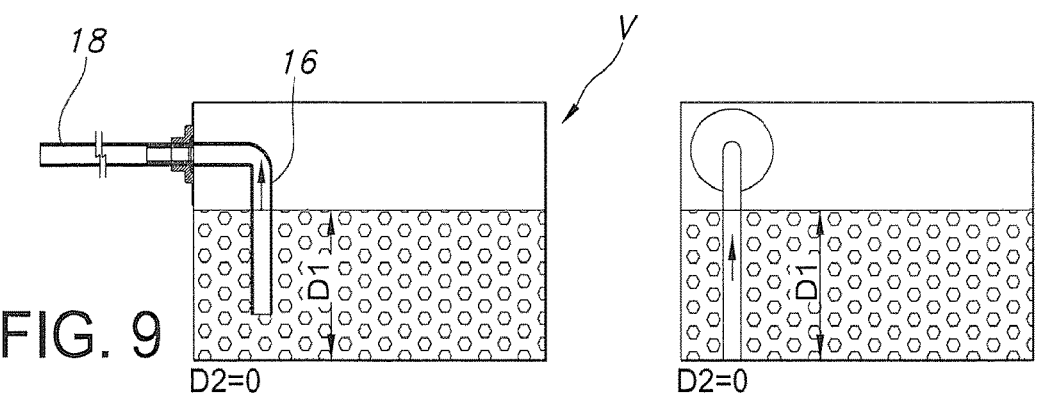
Figure 10:
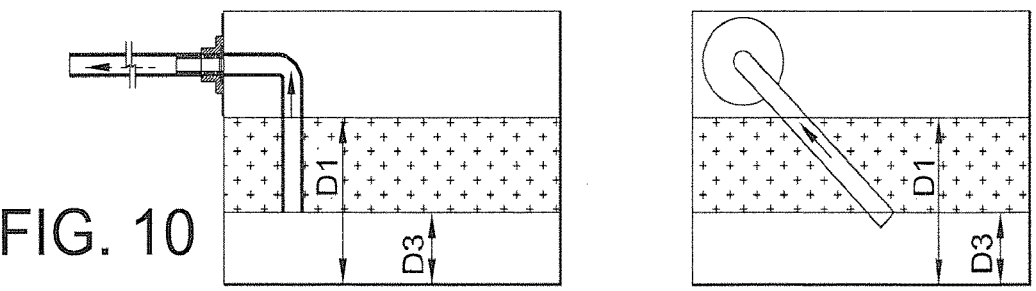

Turning to FIGS. 9 and 10, each of which includes front and end views of a vessel V, it can be appreciated that the adjustable drain 10 disclosed may also be used to achieve the functions normally accomplished using a dip tube. For example, in FIG. 9, the interior drain tube 16 is provided at a position in the upper corner of the vessel V and having a length such that the inlet E is adjacent to or in contact with the floor F. Thus, by using external force, such as applied from a pump, fluid from the interior compartment I may be evacuated from a height $D_1$ all the way down to the floor F, which thus means that the vessel V may be substantially fully drained (that is, $D_2=0$). Alternatively, as shown in FIG. 10, the drain tube 16 may be repositioned to remove the fluid to a particular level $D_3$.

As briefly noted above, it is preferred to make the vessel V and all of its components of disposable materials, such as plastics. In the case where the sidewall W of the vessel V is flexible (meaning it can assume the shape of the fluid in the absence of additional support), the components of the drain 10 are all more rigid that the flexible sidewall W. In any case, the interior drain tube 16 should be sufficiently rigid that the inlet E can be positioned at a known or desired position by rotating the coupler 14.

Figure 11:
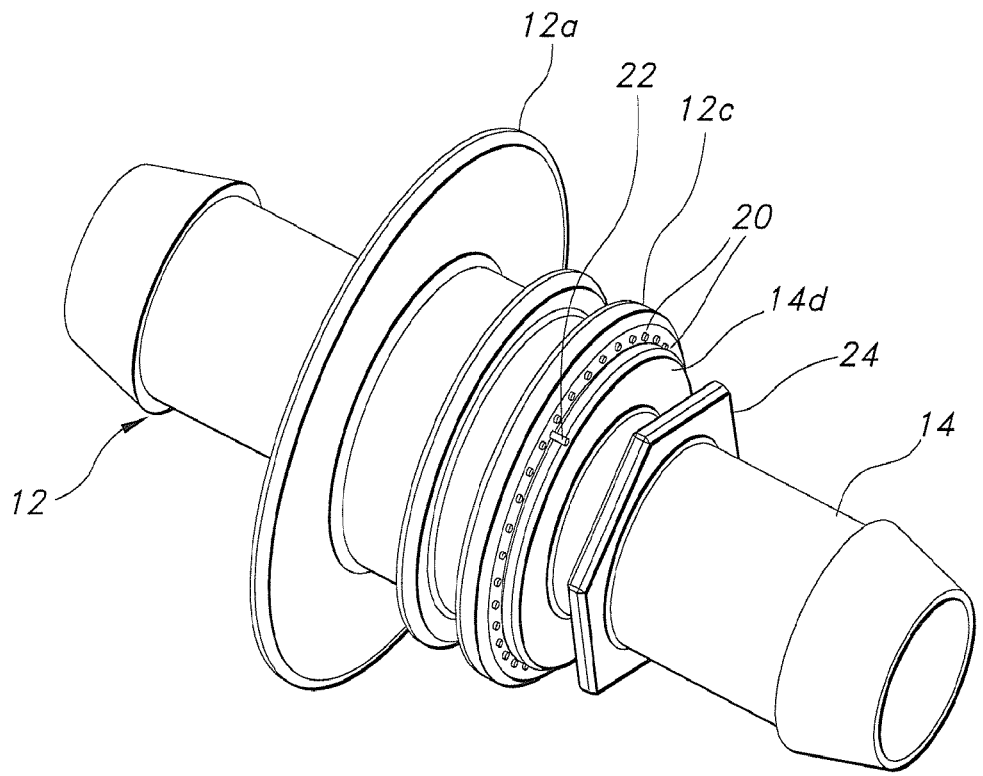
FIG. 11 is a perspective view of an indexing feature that may optionally be provided in association with an adjustable drain.
Figure 12:
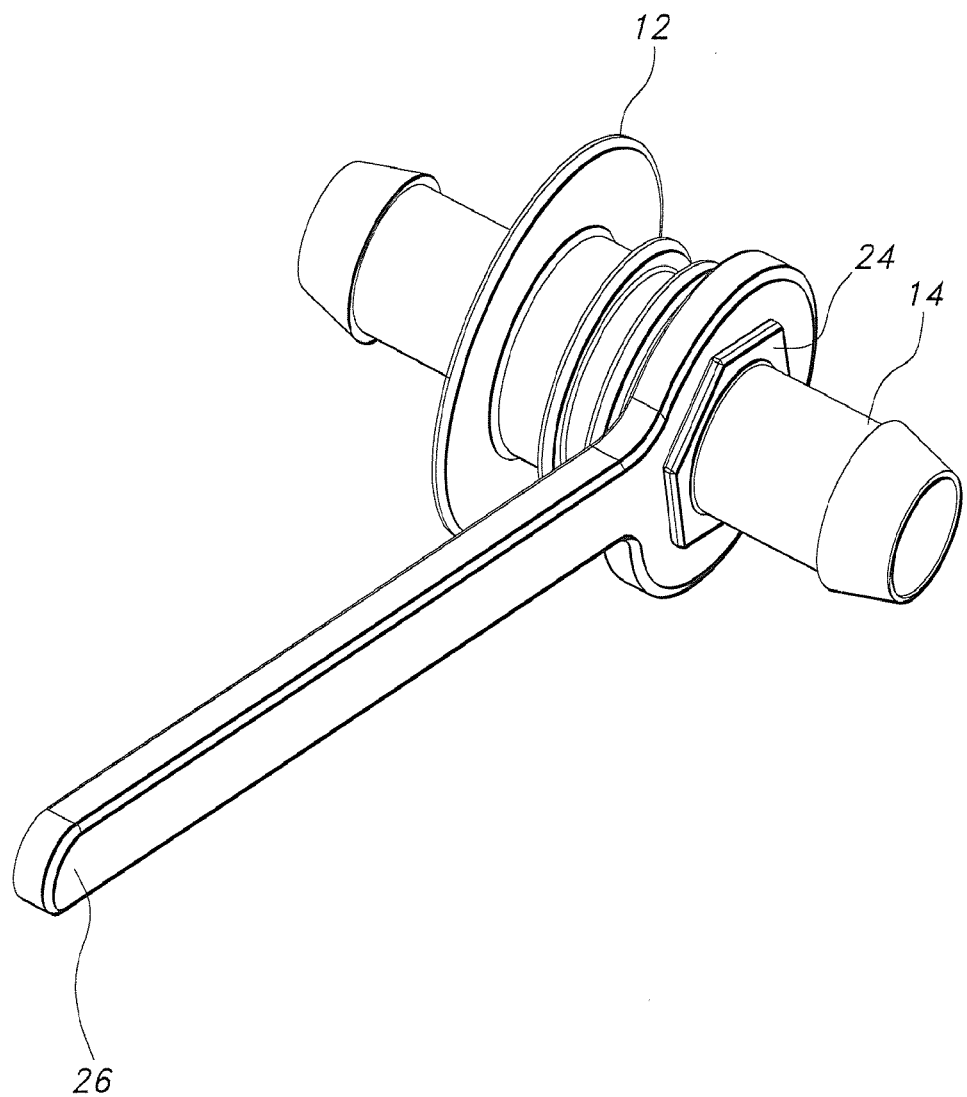
FIG. 12 illustrates a perspective view of a tool used in connection with the adjustable drain of FIG. 11.

FIGS. 11 and 12 are directed to an optional feature that may be used to determine the relative position of a drain tube, such as the angled drain tube 16, from exterior to the interior compartment I. In the illustrated embodiment, this feature comprises means for indexing the position of the interior drain tube 16. Preferably, this means for indexing includes one or more identifications, such as visible markings 20, corresponding to various positions on a structure fixed to the vessel V, such as connector 12 (which is shown including a barb for interfacing with the drain tube 16 in the interior compartment I). These markings 20 may comprise indentations or projections provided at a regular interval around the circumference of a second flange 12c of the connector 12. One or more corresponding indicators 22 may be associated with a part moving in connection with the rotation of the drain tube 16, but external to the interior compartment I (for instance, a flange 14d on coupler 14, which as noted above is rotatably positioned at least partially within connector 12). Frictional engagement between the opposing faces of the second flange 12c and the flange 14d may also help to retard the relative rotational movement of the connector 12, and thus hold the drain tube 16 in the desired position. In the case where the markings 20 comprise projections (such as raised bumps), the indicator 22 may be such that it can be captured and retained by one or more of the projections to restrain the relative movement. Alternatively, the indicator 22 may comprise a bump, and the projections may take the form of mating notches.

As should be appreciated, this indexing feature allows the user to, at a minimum, ascertain the angular position of the inlet E of the drain tube 16 within the interior compartment I. This is true even if this tube cannot be perceived from external to the vessel V, such as due to an opaque material forming the sidewall W or a cloudy fluid in the interior compartment I. The feature may also help to assist in retaining the relative position of the drain tube 16.

FIGS. 11 and 12 together also illustrate another optional feature, which comprises a grip for facilitating the act of rotating the coupler 14. Preferably, the grip comprises a generally polygonal flange 24 adapted for engaging a corresponding tool, such as a wrench 26, to effect rotation of the coupler 14 in the desired manner. This feature allows the user to alter the position of the drain tube 16 in an easy, repeatable, and precise fashion in order to achieve the desired draining objective, such as for draining fluid from a position above or below the connector 12.

In summary, the disclosed adjustable side drain 10 may be used to advantage by allowing the manufacturer to provide a single type of vessel V that simultaneously meets the particular needs or demands of many customers. Advantageously, the need for storing a plurality of specially adapted vessels until an order is made can be eliminated, since the drain 10 may be adjusted to accommodate the needs associated with particular uses. This may not only reduce warehousing and tracking costs, but also the resultant shorter manufacturing time and the lack of involved techniques also helps to enhance efficiency. An optional indexing feature may also be provided to allow the position of the drain tube within the interior compartment of the vessel to be easily and accurately determined.

The foregoing descriptions of various embodiments of the invention are provided for purposes of illustration, and are not intended to be exhaustive or limiting. Modifications or variations are also possible in light of the above teachings. For example, if the angled drain tube 16 need not rotate or move, then the connector 12 could be formed as an integral part and attached to the vessel V. The embodiments described above were chosen to provide the best application to thereby enable one of ordinary skill in the art to utilize the disclosed inventions in various embodiments and with various modifications as are suited to the particular use contemplated. All such modifications and variations are within the scope of the invention.

The invention claimed is:

1. An apparatus for forming a drain in a vessel including a sidewall at least partially defining an interior compartment for receiving a fluid, comprising:
    an angled drain tube for withdrawing fluid from the interior compartment, said drain tube capable of rotating within the interior compartment to a height of a desired fluid level;
    a connector for connecting to the sidewall of the vessel, said connector adapted for supporting the angled drain tube; and
    a plurality of markings provided at intervals around a circumference of the connector, said markings indicating a relative position of the end portion of the drain tube within the interior compartment from exterior to the interior compartment.

2. The apparatus of claim 1, further including a coupler adapted for coupling with a first end of the drain tube.

3. The apparatus of claim 2, wherein the coupler is positioned in the connector.

4. The apparatus of claim 3, further including at least one sealing element for sealing the coupler with the connector.

5. The apparatus of claim 2, further including a drain tube external to the interior compartment, and wherein the coupler is adapted for coupling with the external drain tube.

6. The apparatus of claim 2, wherein the coupler includes a peripheral flange for mating with a recess of the connector.

7. The apparatus of claim 2, wherein the coupler comprises at least one indicator for aligning with at least one of the plurality of markings to indicate the relative position of the drain tube.

8. The apparatus of claim 7, wherein the plurality of markings comprise projections, and the at least one indicator is adapted engage the projections.

9. The apparatus of claim 7, wherein markings comprise notches, and the at least one indicator comprises a projection for engaging the notches.

10. The apparatus of claim 7, wherein an engagement between the markings and the indicator is adapted to retard relative movement between the connector and the drain tube.

11. The apparatus of claim 1, wherein the angled drain tube includes an inlet adapted to rotate within a plane parallel to the sidewall of the vessel.

12. The apparatus of claim 1, wherein the angled drain tube is adapted to rotate substantially 360 degrees.

13. The apparatus of claim 1, wherein the angled drain tube is adapted for rotating about a longitudinal axis.

14. An apparatus for forming a connection with a drain tube external to a vessel including a sidewall at least partially defining an interior compartment for receiving a fluid, said sidewall including a connector, comprising:
   a coupler for forming a sealing engagement with the connector and having a first end adapted for engaging the external drain tube;
   an angled drain tube including an inlet, said drain tube connected to the coupler and for positioning in the interior compartment; and
   at least one indicator associated with the coupler for indicating an angular position of the inlet of the drain tube within the interior compartment from exterior to the interior compartment.

15. An apparatus for use in processing a fluid, comprising:
   a vessel adapted for receiving the fluid, the vessel having a sidewall including a passage and at least partially defining an interior compartment;
   a drain tube for positioning at least partially in the interior compartment and draining fluid therefrom through the passage;
   a connector connected to the sidewall, wherein the drain tube is mounted for rotation relative to the connector, said connector comprising a plurality of markings provided at a regular interval around at least a portion of the connector; and
   a coupler connected to the drain tube, said coupler adapted to rotate with the drain tube relative to the connector, wherein the coupler comprises at least one indicator for indicating a position of the drain tube within the interior compartment from outside the interior compartment based on a relative position between the indicator and one of the plurality of markings.

16. The apparatus of claim 15, wherein the drain tube is connected to the sidewall and extends in the interior compartment, said drain tube including a portion having a longitudinal axis generally aligned with a plane of the sidewall.

17. The apparatus of claim 15, wherein the drain tube is connected to the sidewall and projects into the interior compartment of the vessel.

18. The apparatus of claim 15, wherein the drain tube is connected to the sidewall at a reference point, said drain tube having an inlet adapted for movement between a first position for draining fluid at or above the reference point and a second position for draining fluid at or below the reference point.

19. The apparatus of claim 15, wherein the drain tube is rotatably supported by the sidewall and includes an inlet, wherein rotation of the drain tube relative to the sidewall moves the inlet in a plane parallel to the sidewall.

20. An apparatus for forming a passage for a fluid, comprising:
   a vessel including a wall with an opening forming passage in the wall, said wall at least partially defining an interior compartment for receiving the fluid;
   a drain including a drain tube projecting through the opening and into the interior compartment of the vessel, said tube being arranged to rotate about a longitudinal axis of the drain tube and relative to the wall of the vessel, and an indicator adapted to rotate with the drain tube; and
   a plurality of fixed markings provided at regular intervals with respect to at least a portion of a circumference of the opening, each marking for indicating a relative angular position of the drain tube in the interior compartment;
   wherein the relative position of the indicator with respect to the plurality of markings identifies the position of the drain tube relative to the vessel during rotation.

21. A method of forming a vessel having a sidewall, comprising:
   providing the vessel including a drain tube at least partially within the vessel and connected to the sidewall at a reference point and a plurality of markings with respect to the reference point, said drain tube having an inlet adapted for movement between a first position for draining fluid at or above the reference point and a second position for draining fluid at or below the reference point, and further comprising an indicator for rotation with the drain tube, wherein placement of the indicator at a position with respect to the plurality of markings indicates a position of the inlet.

22. A method of fluid processing, comprising:
   providing a vessel including a drain tube projecting through an opening in a sidewall of the vessel, said drain tube having an inlet positioned in an interior compartment of the vessel, and said drain tube further including an indicator positioned outside the interior compartment of the vessel;
   providing a plurality of markings around at least a portion of a circumference of the opening;
   raising or lowering the inlet to a desired position by rotating the drain tube and aligning the indicator with one of the plurality of markings corresponding to the desired position; and
   draining fluid through the drain tube.

* * * * *